(12) United States Patent
Crnkovich et al.

(10) Patent No.: US 12,714,769 B2
(45) Date of Patent: Aug. 25, 2026

(54) DIALYSIS TREATMENT AND MACHINE

(71) Applicant: Fresenius Medical Care Holdings, Inc., Waltham, MA (US)

(72) Inventors: Martin Joseph Crnkovich, Walnut Creek, CA (US); David Yuds, Hudson, NH (US); Roland Levin, San Ramon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 434 days.

(21) Appl. No.: 18/456,237

(22) Filed: Aug. 25, 2023

(65) Prior Publication Data

US 2025/0018099 A1 Jan. 16, 2025

Related U.S. Application Data

(63) Continuation-in-part of application No. 18/349,522, filed on Jul. 10, 2023.

(51) Int. Cl.
*G16H 20/00* (2018.01)
*A61M 1/16* (2006.01)
*G16H 20/40* (2018.01)

(52) U.S. Cl.
CPC ........ *A61M 1/1603* (2014.02); *A61M 1/1607* (2014.02); *A61M 1/1609* (2014.02);
(Continued)

(58) Field of Classification Search
CPC .............. A61M 1/1603; A61M 1/1607; A61M 1/1609; A61M 1/1613; A61M 1/1615;
(Continued)

(56) References Cited

U.S. PATENT DOCUMENTS 4,386,634 A 6/1983 Stasz et al.
5,486,286 A * 1/1996 Peterson ............. A61M 1/1664 210/90

(Continued)

FOREIGN PATENT DOCUMENTS

CN 104023763 9/2014
EP 2035059 3/2009

(Continued)

OTHER PUBLICATIONS

International Search Report and Written Opinion in International Appln. No. PCT/US2024/036779, mailed Oct. 14, 2024, 19 pages.

(Continued)

*Primary Examiner* — John Kim
(74) *Attorney, Agent, or Firm* — Fish & Richardson P.C.

(57) ABSTRACT

The disclosure relates to a method including determining a treatment time of a dialysis treatment for a patient, receiving, from at least a sensor of a dialysis machine, a dialysate flow rate, the dialysate comprising bicarbonate pumped out of a bicarbonate source, wherein the bicarbonate source has an initial amount of bicarbonate, and predicting that by end of the dialysis treatment no more than a threshold amount of bicarbonate will be left in the bicarbonate source, and in response, determining that a clearance value during the treatment is or will be higher than the threshold clearance value, and sending, to a balancing system, an instruction to reduce the dialysate flow rate to a reduced rate, wherein the reduced rate results in reducing a rate of bicarbonate pumped out of the bicarbonate source while maintaining a clearance value of the treatment at no less than the threshold clearance value.

20 Claims, 6 Drawing Sheets

(52) U.S. Cl.
CPC ........ *A61M 1/1613* (2014.02); *A61M 1/1615* (2014.02); *A61M 1/1619* (2014.02); *A61M 1/1635* (2014.02); *A61M 1/1654* (2013.01); *A61M 1/1656* (2013.01); *G16H 20/00* (2018.01); *G16H 20/40* (2018.01); *A61M 2205/3317* (2013.01); *A61M 2205/3327* (2013.01); *A61M 2205/3334* (2013.01); *A61M 2205/50* (2013.01); *A61M 2205/502* (2013.01)

(58) Field of Classification Search
CPC .............. A61M 1/1619; A61M 1/1635; A61M 1/1654; A61M 1/1656; A61M 2205/3317; A61M 2205/3327; A61M 2205/3334; A61M 2205/50; A61M 2205/502; G16H 20/00; G16H 20/40
See application file for complete search history.

(56) References Cited

U.S. PATENT DOCUMENTS 5,902,476 A 5/1999 Twardowski
10,369,261 B2 8/2019 Jonas et al.
10,668,199 B2 6/2020 Rada et al.
11,123,464 B2 9/2021 Yuds et al.
2006/0054215 A1 3/2006 Remkes et al.
2008/0015487 A1 1/2008 Szamosfalvi et al.
2010/0010426 A1 1/2010 Childers et al.
2010/0010428 A1 1/2010 Yu et al.
2010/0069817 A1 3/2010 Falkvall et al.
2013/0049974 A1 2/2013 Crnkovich et al.
2013/0248426 A1 9/2013 Pouchoulin
2014/0220699 A1* 8/2014 Pudil ...................... G01N 33/84 436/163
2014/0263064 A1 9/2014 Jones et al.
2015/0034536 A1 2/2015 Rada et al.
2015/0034557 A1 2/2015 Pouchoulin
2016/0101278 A1 4/2016 Norris et al.
2016/0216150 A1 7/2016 Groeber et al.
2017/0224897 A1* 8/2017 Kopperschmidt .. A61M 1/1617
2017/0265793 A1 9/2017 Maierhofer
2017/0304519 A1 10/2017 Jonas et al.
2017/0319768 A1 11/2017 Szpara et al.
2017/0326284 A1 11/2017 Dulsner et al.
2018/0093027 A1 4/2018 Oppegard et al.
2019/0388600 A1 12/2019 Yuds et al.
2020/0061273 A1 2/2020 Hogard et al.
2020/0179583 A1 6/2020 Hobot et al.
2020/0294676 A1* 9/2020 Cherif .................... G16C 10/00
2022/0001086 A1 1/2022 Yuds et al.
2023/0201432 A1 6/2023 Doyle et al.
2024/0123127 A1* 4/2024 Rovatti ............... A61M 1/3612

FOREIGN PATENT DOCUMENTS

EP 3335742 6/2018
WO WO 2007/144427 12/2007
WO WO 2020/076945 4/2020

OTHER PUBLICATIONS

Glickman et al., "Choosing home hemodialysis for end-stage kidney disease," Feb. 7, 2023, retrieved on Sep. 14, 2023, retrieved from URL <https://www.uptodate.com/contents/home-hemodialysis>, 1 page.
International Preliminary Report on Patentability in International Appln. No. PCT/US2019/037424, mailed Dec. 30, 2020, 7 pages.
International Search Report and Written Opinion in Appln. No. PCT/US2019/037424, dated Sep. 10, 2019, 9 pages.
International Search Report and Written Opinion in Appln. No. PCT/US2022/053387, mailed Mar. 21, 2023, 12 pages.
UnitedHealthcare, "Home Hemodialysis (for North Carolina Only)," Jul. 1, 2023, retrieved on Sep. 14, 2023, retrieved from URL <https://www.uhcprovider.com/content/dam/provider/docs/public/policies/medicaid-comm-plan/nc/home-hemodialysis-nc-cs.pdf>, 11 pages.
Weinhandl, "Standardized Kt/V on Home Hemodialysis: Does It Matter?," Apr. 23, 2018, retrieved on Sep. 14, 2023, retrieved from URL <https://advancingdialysis.org/standardized-kt-v-home-hemodialysis-matter/>, 3 pages.
International Preliminary Report on Patentability in International Appln. No. PCT/US2022/053387, mailed Jul. 11, 2024, 7 pages.
International Preliminary Report on Patentability in International Appln. No. PCT/US2024/036779, mailed on Jan. 22, 2026, 10 pages.

* cited by examiner

DIALYSIS TREATMENT AND MACHINE

CROSS-REFERENCE TO RELATED APPLICATIONS

This application is a continuation-in-part application of and claims the benefit of priority to U.S. application Ser. No. 18/349,522, filed on Jul. 10, 2023, the contents of which are hereby incorporated by reference.

TECHNICAL FIELD

This disclosure is related to dialysis machines and methods. In particular, disclosure covers methods of maintaining one or more dialysis sources (e.g., a source of bicarbonate) within a specific threshold value throughout the treatment.

BACKGROUND

Dialysis is often prescribed for patients who are unable to clear his or her blood properly using his or her renal system (e.g., kidneys).

The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream across the membrane. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

In an HD treatment, a patient is connected to an extracorporeal blood circuit by inserting a venous bloodline and an arterial bloodline to draw intoxicated blood from the body and infuse the cleaned blood back into the body. A dialysis machine takes in the blood from the arterial line, and flows the blood past a semipermeable membrane or filter that is permeable to toxins and fluid. On the other side of the filter, dialysate flows in the opposite direction. The dialysate is a combination of acid, water, and other chemicals, the most notable of which is bicarbonate. The length of treatment time and concentrations of chemicals within the dialysate are prescribed by a physician and are inputted into the dialysis machine prior to beginning dialysis. The prescription includes a concentration of bicarbonate, flow rate, and treatment length, among other parameters and concentrations. Often the dialysate is mixed using fluids that are previously saturated with a specific substance. For example, bicarbonate solution is created by mixing fluid with powder bicarbonate concentrate. That bicarbonate solution can then be used to mix with other saturated solutions to create dialysate.

The saturated solution for a single substance can be readied by the machine by inserting a container into the dialysis machine and inputting all relevant information including the size of the container, the prescription, and additional patient data. The larger volume containers are able to support longer treatment sessions and/or increased flow rates. After initial connection to the machine, the dialysis machine fills the bags with water, dissolving the powdered bicarbonate, and creating a bicarbonate solution. The dialysis machine then moves the saturated bicarbonate solution to mix with acid solution and additional substances in a chamber, to create dialysate. After some of the solution is removed from the container, additional bicarbonate solution is generated to in turn, produce more dialysate. These containers are considered depleted when the bicarbonate or acid concentrate is depleted. Current machines test depletion of bicarbonate using conductivity sensors. To determine the proper volume of container, the patient or operator consults a manual for a table that provides an approximate depletion time based on the prescribed flow rate and the prescribed bicarbonate concentration. An alarm or other form of user notification will occur when the bicarbonate level or the acid level is below, for example, 20%. When this occurs, the treatment is paused and the operator changes one or both containers in order to proceed with treatment. It is preferred to ensure the bicarbonate or acid will last the entire treatment, to prevent stoppage of the treatment.

In use, an operator prepares the dialysis machine and the patient prior to enacting the treatment, which can be a time consuming process. It involves disinfecting the machine, the patient, and all apparatus interacting with the machine or the patient. A mistake in the setup may not be apparent until an alarm triggers during dialysis, if the dialysis machine is configured to test for these mistakes.

SUMMARY

This disclosure covers techniques to adjust the flow rate of material(s) retrieved from dialysis resource(s) (e.g., bicarbonate, acid concentrate, etc.) to extend the time of running the treatment before having to refill the resource. The techniques include determining or predicting that a particular treatment resource attached to a dialysis machine will run below a specific threshold value before the treatment ends, and make the proper adjustment to extend the time of running the treatment while using the available resource. The techniques make sure that changing the flow rate would not degrade the treatment clearance value unacceptably. For example, the techniques involve projecting the clearance value throughout the treatment, and making sure that the clearance value does not fall below a specific clearance threshold value.

The details of one or more embodiments are set forth in the accompanying drawings and the description below. Other aspects, features, and advantages of the disclosure will be apparent from the description and drawings, and from the claims.

Some implementations include a computer-implemented method executable by a processor of a dialysis machine, wherein the method includes determining, based on a prescription received from an external source, a treatment time of a dialysis treatment for a patient, receiving, from at least a first sensor of the dialysis machine, a dialysate flow rate of dialysate running in the machine, the dialysate including bicarbonate pumped out of a bicarbonate source attached to the dialysis machine, wherein the bicarbonate source has an initial amount of bicarbonate before the dialysis treatment starts, and predicting, based on (i) the treatment time, (ii) the initial amount of bicarbonate, and (iii) the dialysate flow rate, that by end of the dialysis treatment no more than a specific threshold amount of bicarbonate will be left in the bicarbonate source. In response, the method can include determining that a clearance value during the treatment is or will be higher than a specific threshold clearance value, and sending, to a balancing system that receives the dialysate, an instruction to change a switching rate to reduce the dialysate flow rate to a reduced rate, the balancing system being part of the dialysis machine, wherein the reduced rate results in reducing a rate of bicarbonate pumped out of the bicarbonate source while maintaining a clearance value at no less than the clearance threshold value.

Embodiments can include one or any combination of two or more of the following features.

The determined clearance value is or is determined based on a current clearance value of the treatment, and the method further includes determining the current clearance value by receiving, from multiple sensors, measurements of respective conductivity values of the dialysate running to or from a dialyzer of the dialysis machine, and calculating the current clearance value based on the received conductivity values.

The determined clearance value is a future clearance value, and the method further includes predicting the future clearance value by calculating multiple clearance values for the treatment over a time period during the treatment, each clearance value in the multiple clearance values being calculated based on respective conductivity values of the dialysate at a respective time during the time period, predicting, based on a trend in the multiple clearance values and the current clearance value, a future clearance value for a time before the treatment ends.

The method includes generating the instruction to the balancing system based on the predicted future clearance value, wherein the instruction includes a reduction value in the switching rate, wherein the reduction value depends on a difference between the predicted future clearance value and the specific threshold clearance value such that a higher difference causes a higher reduction value.

The instruction is a first instruction, and the method further includes determining that the predicted future clearance value is less than the specific clearance threshold value, and in response, sending, to the balancing system, a second instruction to increase the dialysate rate so that the clearance value of the treatment increases, the second instruction being sent subsequent to sending the first instruction.

The method includes sending the predicted future clearance value to be presented on a display.

The instruction to change the switching rate includes a rate reduction amount for the switching rate.

The method includes determining that the treatment has ended and the machine has been detached from the patient, and in response, sending, to the balancing system, a post-treatment instruction to reduce the dialysate flow rate.

The post-treatment instruction includes an instruction to reduce the dialysate flow rate to less than half.

Some implementations include a dialysis system that includes a dialyzer, a fluid line for passing dialysate from a bicarbonate source to a balancing system, a sensor configured to measure a dialysate flow rate of dialysate running in the fluid line, the dialysate including bicarbonate pumped out of the bicarbonate source, the balancing system configured to transfer clean dialysate from the fluid line to the dialyzer, and drain used dialysate from the dialyzer to a drainage, wherein the balancing system includes a switch with a status that changes with a switch rate, wherein a change in the switch rate causes a change in the dialysis flow rate running through the fluid line, and a processor configured to perform operations. The operations include determining, based on a prescription received from an external source, a treatment time of a dialysis treatment for a patient, receiving, from the sensor, the dialysate flow rate, wherein the bicarbonate source has an initial amount of bicarbonate before the dialysis treatment starts, predicting, based on (i) the treatment time, (ii) the initial amount of bicarbonate, and (iii) the dialysate flow rate, that by end of the dialysis treatment no more than a specific threshold amount of bicarbonate will be left in the bicarbonate source, and in response, determining that a clearance value during the treatment is or will be higher than a specific threshold clearance value, and sending, to the balancing system, an instruction to change the switching rate to reduce the dialysate flow rate to a reduced rate, wherein the reduced rate results in reducing a rate of bicarbonate pumped out of the bicarbonate source while maintaining a clearance value at no less than the threshold clearance value.

Embodiments can include one or any combination of two or more of the following features.

The dialysis system includes multiple sensors operatively connected to the fluid line of the dialysis machine, the multiple sensors being configured to measure respective conductivity values of the dialysate running to or from the dialyzer.

The determined clearance value is or is determined based on a current clearance value of the treatment, and the operations further include determining the current clearance value by receiving, from the multiple sensors, the respective conductivity values, and calculating the current clearance value based on the received conductivity values.

The determined clearance value is a future clearance value, and the operations further include predicting the future clearance value by calculating multiple clearance values for the treatment over a time period during the treatment, each clearance value in the multiple clearance values being calculated based on respective conductivity values of the dialysate at a respective time during the time period, and predicting, based on a trend in the multiple clearance values and the current clearance value, a future clearance value for a time before the treatment ends.

The operations further include generating the instruction based on the predicted value, wherein the instruction includes a reduction value in the switching rate, wherein the reduction value depends on a difference between the predicted future clearance value and the specific threshold clearance value such that a higher difference causes a higher reduction value.

The instruction is a first instruction, and the operations further include determining that the predicted future clearance value is less than the specific threshold clearance value, and in response, and sending, to the balancing system, a second instruction to increase the dialysate rate so that the clearance value of the treatment increases, the second instruction being sent subsequent to sending the first instruction.

The operations include sending the predicted future clearance value to display to be presented on the display.

The instruction to change the switching rate includes a rate reduction amount for the switching rate.

Some implementations include one or more computer readable media storing instructions that are executable by a processing device, and upon such execution cause the processing device to perform operations include determining, based on a prescription received for a patient from an external source, a treatment time of a dialysis treatment for the patient, receiving, from at least a sensor of the dialysis machine, a dialysate flow rate of dialysate running in the machine, the dialysate including bicarbonate pumped out of a bicarbonate source attached to the dialysis machine, wherein the bicarbonate source has an initial amount of bicarbonate before the treatment starts, predicting, based on (i) the treatment time, (ii) the initial amount of bicarbonate, and (iii) the dialysate flow rate, that by end of the dialysis treatment no more than a specific threshold amount of bicarbonate will be left in the bicarbonate source, and in response, determining that a clearance value during the treatment is or will be higher than a specific threshold clearance value, and sending, to a balancing system that receives the dialysate, an instruction to change a switching rate to reduce the dialysate flow rate to a reduced rate, the balancing system being part of the dialysis machine, wherein the reduced rate results in reducing a rate of bicarbonate pumped out of the bicarbonate source while maintaining a clearance value at no less than the threshold clearance value.

Embodiments can include one or any combination of two or more of the following features.

The determined clearance value is a future clearance value, and the operations further includes predicting the future clearance value by, calculating multiple clearance values for the treatment over a time period during the treatment, each clearance value in the multiple clearance values being calculated based on respective conductivity values of the dialysate at a respective time during the time period, and predicting, based on a trend in the multiple clearance values and the current clearance value, a future clearance value for a time before the treatment ends.

The operations further include generating the instruction based on the predicted value, wherein the instruction includes a reduction value in the switching rate, wherein the reduction value depends on a difference between the predicted future clearance value and the specific threshold clearance value such that a higher difference causes a higher reduction value.

Some implementations include a computer-implemented method executable by a processor of a dialysis machine, wherein the method includes determining, based on a prescription received from an external source, a treatment time of a dialysis treatment for a patient; receiving, from at least a sensor of the dialysis machine, a dialysate flow rate of dialysate running in the dialysis machine, the dialysate comprising bicarbonate pumped out of a bicarbonate source attached to the dialysis machine, wherein the bicarbonate source has an initial amount of bicarbonate before the dialysis treatment starts; and predicting, based on (i) the treatment time, (ii) the initial amount of bicarbonate, and (iii) the dialysate flow rate, that by end of the dialysis treatment no more than a specific threshold amount of bicarbonate will be left in the bicarbonate source. The method can also include, in response to predicting that by end of the dialysis treatment no more than a specific threshold amount of bicarbonate will be left in the bicarbonate source, determining that a clearance value during the treatment is or will be higher than a specific threshold clearance value, and sending, to a balancing system that receives the dialysate, an instruction to change a switching rate to reduce the dialysate flow rate to a reduced rate, the balancing system being part of the dialysis machine. The reduced rate can result in reducing a rate of bicarbonate pumped out of the bicarbonate source while maintaining a clearance value of the treatment at no less than the threshold clearance value.

Some implementations include a dialysis system comprising: a dialyzer; a fluid line for passing dialysate from bicarbonate source to a balancing system; a sensor configured to measure a dialysate flow rate of dialysate running in the fluid line, the dialysate comprising bicarbonate pumped out of the bicarbonate source; the balancing system configured to transfer clean dialysate from the fluid line to the dialyzer, and drain used dialysate from the dialyzer to a drainage, wherein the balancing system comprises a switch with a status that changes with a switch rate, wherein a change in the switch rate causes a change in the dialysis flow rate running through the fluid line; and a processor. The processor can be configured to perform operations comprising: determining, based on a prescription received from an external source, a treatment time of a dialysis treatment for a patient; receiving, from the sensor, the dialysate flow rate, wherein the bicarbonate source has an initial amount of bicarbonate before the dialysis treatment starts; predicting, based on (i) the treatment time, (ii) the initial amount of bicarbonate, and (iii) the dialysate flow rate, that by end of the dialysis treatment no more than a specific threshold amount of bicarbonate will be left in the bicarbonate source, and in response, determining that a clearance value during the treatment is or will be higher than a specific threshold clearance value, and sending, to the balancing system, an instruction to change the switching rate to reduce the dialysate flow rate to a reduced rate. The reduced rate results in reducing a rate of bicarbonate pumped out of the bicarbonate source while maintaining a clearance value of the treatment at no less than the threshold clearance value.

Some implementations include one or more computer readable media storing instructions that are executable by a processing device. Upon such execution the instructions cause the processing device to perform operations comprising: determining, based on a prescription received for a patient from an external source, a treatment time of a dialysis treatment for the patient; receiving, from at least a sensor of the dialysis machine, a dialysate flow rate of dialysate running in the dialysis machine, the dialysate comprising bicarbonate pumped out of a bicarbonate source attached to the dialysis machine, wherein the bicarbonate source has an initial amount of bicarbonate before the dialysis treatment starts; predicting, based on (i) the treatment time, (ii) the initial amount of bicarbonate, and (iii) the dialysate flow rate, that t by end of the dialysis treatment no more than a specific threshold amount of bicarbonate will be left in the bicarbonate source, and in response, determining that a clearance value during the treatment is or will be higher than a specific threshold clearance value, and sending, to a balancing system that receives the dialysate, an instruction to change a switching rate to reduce the dialysate flow rate to a reduced rate, the balancing system being part of the dialysis machine. The reduced rate results in reducing a rate of bicarbonate pumped out of the bicarbonate source while maintaining a clearance value of the treatment at no less than the threshold clearance value.

BRIEF DESCRIPTION OF THE FIGURES

Like reference symbols in the various drawings indicate like elements.

DETAILED DESCRIPTION

To avoid having to pause a treatment to refill or change a supply source (e.g., a bicarbonate bag or bibag), it is preferred to make sure that enough of the supply is available to the dialysis machine before starting the treatment. However, each treatment has its specific parameters and may use an amount of the supply different from another treatment. It would be cumbersome, time consuming (which would delay the current and the consecutive treatment processes), and prone to error for the operators to calculate the amount of each supply needed for each treatment. It would also cause wasting the supply when the supply source is not completed depleted before the treatment starts, but is determined to run short before the treatment ends.

The present disclosure provides techniques to use as much of the supply source as possible before having to replace or refill the source. The techniques also provides for reducing the chance of having to pause the treatment to refill or change the supply source.

Figure 1:
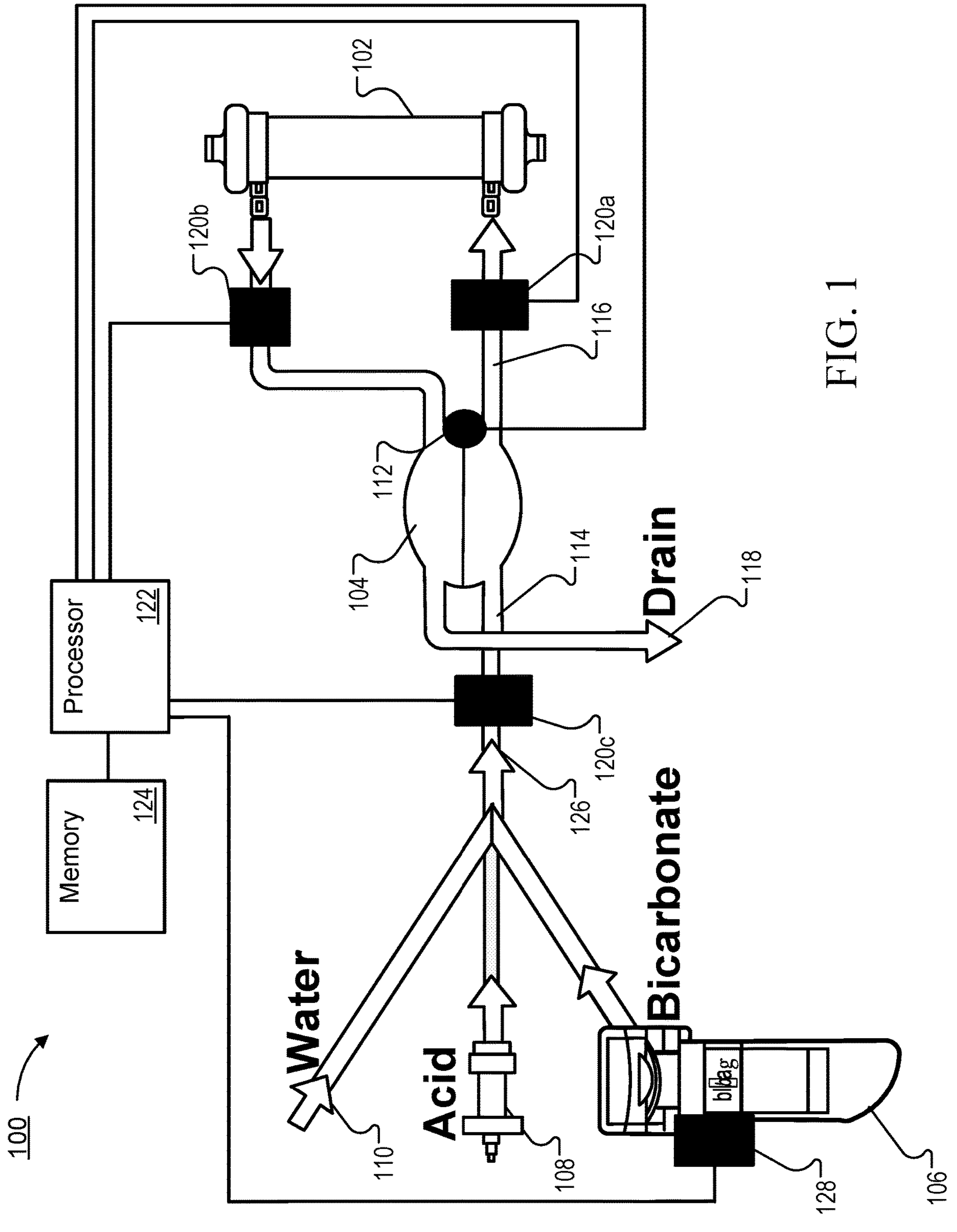
FIG. 1 is a schematic of a dialysis system.

FIG. 1 schematically illustrates a dialysis system 100 including a dialyzer 102, a balancing system 104, a bicarbonate concentrate source 106, an acid source 108, and a water source 110. The balancing system 104 is fluidly connected to the bicarbonate concentrate source 106, the acid source 108, and the water source 110. Bicarbonate concentrate from the bicarbonate concentrate source 106, acid from the acid source 108, and water from the water source 110 can be mixed to produce dialysate. The dialysate can be used to perform dialysis, as discussed herein.

The balancing system 104 receives the dialysate and controls a dialysate flow rate. For example, a switch 112 can change a switching rate of the balancing system 104 to reduce the dialysate flow rate to a reduced rate or to increase the dialysate flow rate to an increased rate. The switch 112 can be located at a location appropriate to control the switching rate of the balancing system 104; for example, the switch can be located at an input 114 of the balancing system 104, at an output 116 of the balancing system 104, within the balancing system 104, etc.

A status of the switch 112 can change the switching rate of the balancing system 104. For example, the status of the switch 112 can include binary statuses, such as on and off, open and shut, increased rate and decreased rate, etc. In other implementations, the switch 112 can include other statuses, such as linear statuses to control the switching rate linearly.

The dialyzer 102 receives dialysate from the balancing system 104, for example, at a dialysate flow rate defined by the switching rate of the balancing system 104. A semipermeable membrane in the dialyzer separates the blood from the dialysate within the dialyzer and allows diffusion and osmosis exchanges to take place between the dialysate and the blood stream across the membrane. These exchanges across the membrane result in the removal of waste products, including solutes like urea and creatinine, from the blood. These exchanges also regulate the levels of other substances, such as sodium and water, in the blood. The balancing system 104 receives the used dialysate from the dialyzer 102, and directs the used dialysate into a waste receptacle 118.

Sensors 120*a*, 120*b* are arranged between the balancing system 104 and the dialyzer 102. A sensor 120*c* is arranged on a fluid line 126 that connects the balancing system 104 to the bicarbonate source 106, the acid source 108, and the water source 110. The sensors 120*a*, 120*b*, 120*c* can include flow rate sensors to measure a dialysate flow rate of dialysate, or can include other sensors (e.g., pressure sensor) that can measure other characteristics of the dialysis flow used to determine the flow rate of the dialysate. The dialysate flow rate can be increased or decreased as discussed above.

In some implementations, the dialysis machine is configured to determine or receive the volume of a supply source, for example, a container of bicarbonate concentrate attached to the dialysis machine for the production of dialysate. The dialysis machine is also configured to detect the time (referred to as "depletion time") at which bicarbonate concentrate will be depleted or will run below a specific threshold volume, by using the volume determination, the measured flow rate, and the prescription inputted into the dialysis machine. In some implementations, the prescription includes details of the treatment process such as flow rate, minimum clearance value, etc.

The dialysis machine is configured to compare the calculated depletion time with the details included in the prescription, e.g., the prescribed treatment time. As pausing the dialysis is undesired, the depletion time should be a greater time length than the prescribed treatment time, to avoid replacing the bicarbonate container mid-treatment. The dialysis machine compares the length of depletion time and the length of treatment time. The treatment can continue as normal when the depletion time is greater than the treatment time. The dialysis machine will notify or alert the user when the depletion time is less than the treatment time.

The dialysis machine is configured to change one or more characteristics of the treatment process to prolong the depletion time. For example, the dialysis machine can reduce the dialysate rate to reduce the rate of using the resources collected from any or all of bicarbonate source 106, the acid source 108, or the water source 110.

In some implementations, the dialysis machine maintains the clearance value of the treatment above a specific value while or after reducing the flow rate. The current or projected clearance value can be measured or predicted based on conductivity of the dialysate that enters dialyzer 102, and conductivity of the used dialysate that leaves dialyzer 102.

Dialysis machine 100 can include multiple conductivity sensors. In some implementations, sensors 120*a*, 120*b*, 120*c* can also include conductivity sensors to measure a conductivity of the dialysate. In some implementations, the conductivity sensor(s) are separate and/or distinct from the flow rate sensors.

The conductivity of the dialysate can be used to determine the clearance value (e.g., the efficacy) of the treatment. For example, the clearance value (Kt/v) can be a value calculated as the product of urea clearance (K) and time (t) divided by the volume (v) of the fluid passing through the fluid line over the time.

The clearance value of a treatment is an indicator of how well the treatment is proceeding. A higher clearance value means that the treatment—i.e., the dialyzing—is going faster. But it also indicates that the resources attached to the dialyzing machine are being used in a faster speed. There is a tradeoff between the treatment time and the rate of using the resources. A minimum threshold value can be set for the clearance value to make sure that the treatment does not unreasonably prolong by going below that threshold value. In some implementations, the threshold value is included as part of the treatment prescription. In some implementations, a default threshold value is set in case no minimum clearance value is recommended or prescribed by a health provider of the patient going through the treatment.

In some implementations, a clearance value can be measured by introducing a sodium bolus into the dialysate entering the dialyzer 102. The conductivity of the dialysate (including the sodium bolus) can be measured before the dialysate enters the dialyzer 102, e.g., by a first sensor 120*a*. While the dialysate is in the dialyzer 102, diffusion and osmosis exchanges take place between the dialysate and the blood stream across the membrane. When the dialysate exits the dialyzer 102, none, some, or all of the sodium bolus may remain in the used dialysate, depending on how much sodium is absorbed by the blood of the patient. A higher amount of sodium absorbed by the user corresponds to a higher clearance value, for example, due to higher urea clearance. A lower amount of sodium absorbed by the user corresponds to a lower clearance value, for example, due to a low urea clearance. The conductivity of the used dialysate can be measured when the used dialysate is output from the dialyzer 102, e.g., by the second sensor 120*b*, to determine the amount of sodium absorbed by the blood of the patient. For example, the difference between the conductivity of the dialysate (e.g., measured by the first sensor 120*a*) and the conductivity of the used dialysate (e.g., measured by the second sensor 120*b*) can correspond to the amount of sodium absorbed by the blood of the patient.

Referring back to FIG. 1, a processor 122 is operatively connected to the switch 112 and to the sensors 120*a*, 120*b*, 120*c* to receive signals from the sensors 120*a*, 120*b*, 120*c* and control the switch 112. In some implementations, a memory (124) is operatively connected to the processor 122 and stores instructions for the processor to perform operations. In some implementations, the memory is part of the processor, e.g., part of the processor chip.

In some implementations, the processor 122 can conserve the resources of dialysis treatment by reducing, e.g., the flow rate of bicarbonate concentrate into the balancing system 104. For example, the processor can directly reduce the flow rate of bicarbonate concentrate from the bicarbonate concentrate source 106 to the balancing system 104. Similarly, the processor can directly reduce the flow rate of acid from the acid source 108 to the balancing system 104.

The processor 122 can send instructions to control the status of the switch 112, e.g., to control the switching rate of the balancing system 104 and thereby manage the dialysis flow rate to reduce the rate of using dialysis resources, e.g., bicarbonate. The processor can also monitor or project the conductivity, and thereby the clearance value of the treatment, and thereby reduce the flow rate up to an amount that does not cause the clearance value to fall below a specific threshold value.

For example, the processor 122 can receive signals from the sensors 120*a*, 120*b* representing the conductivity of the dialysate and the used dialysate. The processor 122 can determine a current clearance value of the treatment based on the measured conductivity by using the formula Kt/V.

The processor 122 can also determine a projected clearance value based on the determined clearance value and the time of treatment, as will be discussed further below. In some implementations, the processor 122 can receive multiple clearance value measurements. The processor 122 can determine whether the projected clearance value meets or exceeds a clearance threshold value. For example, the clearance threshold value can be provided by a prescription for the patient. If the projected clearance value exceeds the clearance threshold value, the processor 122 can change the status of the switch 112 to reduce the dialysis flow rate (e.g., by changing the switching rate of the balancing system 104).

The processor 122 can send an instruction to the switch 112 to reduce the dialysis flow rate while making sure that the projected clearance value does not fall below the threshold clearance value. Staying close to (e.g., within a predetermined specific range of) or meeting the clearance threshold value, rather than exceeding the clearance threshold value without any limits, can provide a treatment that meets the prescription of the patient while conserving the resources of the dialysis treatment (e.g., water, acid, bicarbonate concentrate, and other chemicals). As noted above, reducing the dialysis flow rate reduces the amount of dialysate used during the treatment. Reducing the amount of dialysate used during the treatment reduces the amount of resources used to form the dialysate, and results in conserving those resources. Conserving the resources used for dialysis treatment increases the likelihood that the resources will last an entire treatment (or several treatments).

In some implementations, the processor can send an instruction to controllable valve 128 to reduce the bicarbonate flow rate from the bicarbonate source. For example, the dialysate flow rate could remain the same, and the bicarbonate flow rate can be reduced to directly reduce the amount of bicarbonate being used.

In some implementations, the dialysis machine is configured to determine a projected clearance value based on a number of clearance value measurements performed over a period of time. For example, the efficacy of a dialysis treatment can be can be measured as a clearance value determined periodically during the treatment. In some implementations, the clearance value measurements are recalculated at intervals. The clearance value measurements may be recalculated using a conductivity sensor, or additional sensors. The clearance value measurements can be used to determine a projected clearance value at the end of treatment. If the projected clearance value is higher than a threshold clearance value, then a dialysate flow rate can be reduced to lower the projected clearance value.

In some implementations, the dialysis machine can reduce dialysate flow during specific portions of the dialysis treatment during which relatively little dialysate and/or low clearance value is needed. For example, the dialysis machine can reduce dialysate flow during pre-treatment setup and/or during post-treatment protocols.

In some implementations, the dialysis machine can determine that treatment has ended and the machine has been detached from the patient. For example, the dialysis machine can determine that treatment has ended based on sensor measurements that indicate a change of pressure on the tubing that is attached to the patient during treatment or indicate a significant reduction (e.g., a stop) in blood flow rate flowing through the dialyzer. In some implementations, the dialysis machine can reduce the dialysate flow rate to less than half of a current dialysate flow rate during pre or post-treatment processes.

In some implementations, the processor can retrieve a current switching rate, for example, from a sensor in the balancing system. The processor can send a second switching rate to the balancing system based on the projected clearance value. The difference between the current switching rate and the second switching rate can be a reduction amount for reducing the switching rate in the balancing system.

The projected clearance value and/or the current clearance threshold value can be displayed on a user interface. The user interface can be located on the dialysis machine. In some implementations, the time elapsed in the treatment time and the time remaining in treatment time can be displayed on the user interface. In some implementations, a graphical or visual measure of projected clearance value and clearance threshold value is displayed on the user interface.

Figure 2:
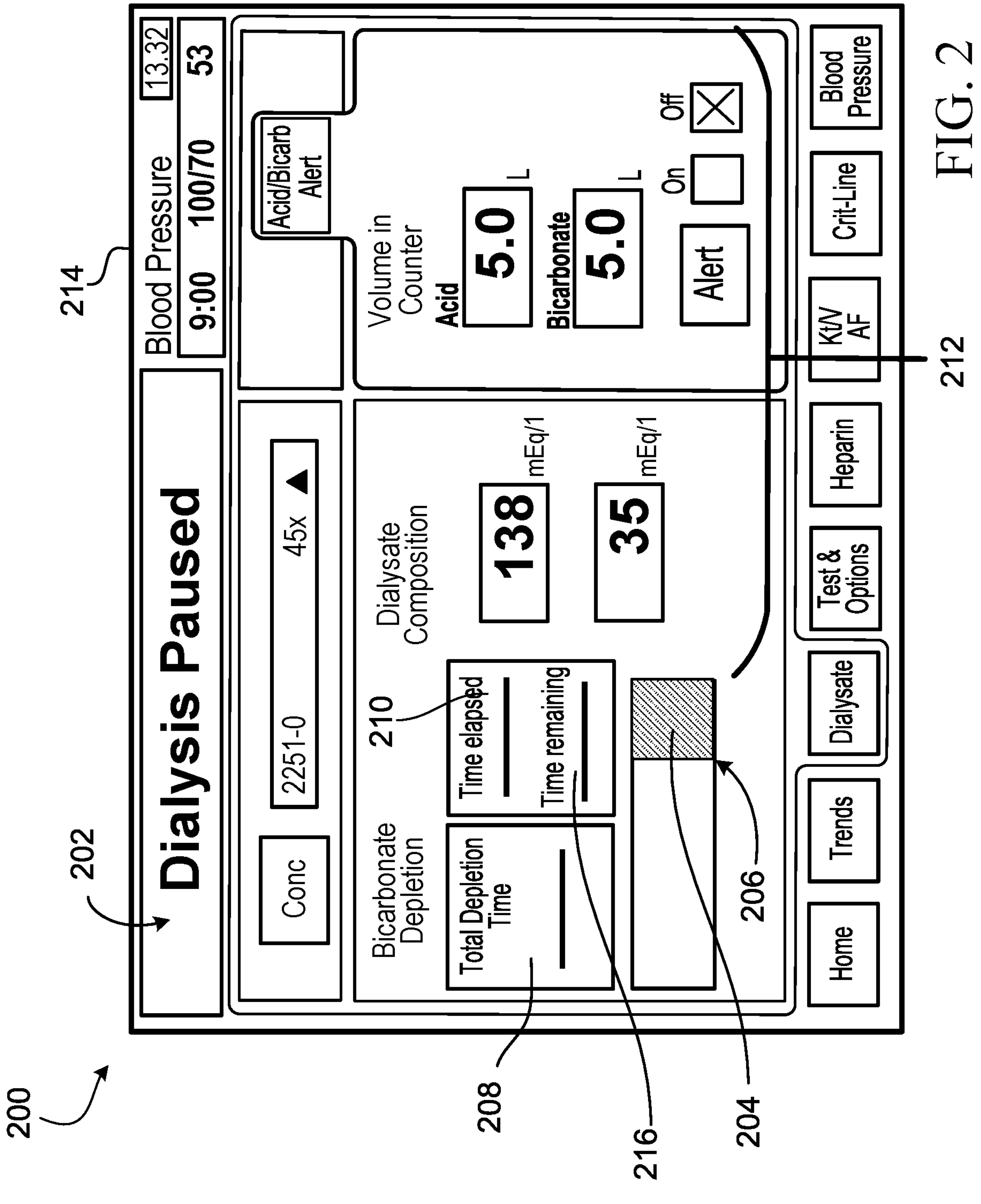
FIG. 2 is a diagram of user interface displaying the dialysate concentrations and the calculated depletion times.

FIG. 2 illustrates an example a user interface 200 of a dialysis machine. The user interface 200 is configured to display information related to the dialysis treatment. For example, the user interface 200 can be a primary interface for user interaction and notifications. The interface can display a notification (e.g., 202) to indicate alert, such as a pause in the dialysis treatment.

At the user interface in FIG. 2, details of a prescription are entered in prescription interface 212. For example, the prescription interface 212 can indicate a volume of a bicarbonate concentrate container, a volume of an acid container, a dialysate composition, a treatment time, and/or a clearance threshold value specified in a prescription for a particular patient. The user interface 200 also shows blood pressure 214, in addition to other treatment and patient information.

The user interface 200 displays the depletion time left 208 (e.g., the treatment time calculated for a determined or provided container volume) in a dialysis treatment. The depletion time 208 can be used to determine a projected clearance value, as discussed below. The time elapsed 210 in the treatment and the time remaining in the treatment 216 are displayed next to the total depletion time 208. Those times can be adjusted based on the prescription details, the dialysate flow rate, the current and/or projected clearance value, etc. throughout the treatment. Additionally, a visual image of depletion or treatment time is displayed. The example visual image shown in FIG. 2 includes a bar 204 that defines the total treatment time, and a highlighted portion 206 of the bar 204 to note the amount of time elapsed.

One or more of the display indicators can be removed or hidden from the displayed user interface. For example, a graphical treatment time representation (e.g., 204/206) or a text-based representation (e.g., 201/216) may be hidden, for example, to simplify the display. The representations and indicators on the user interface can be updated as the dialysis treatment continues to ensure accurate information.

Figure 3:
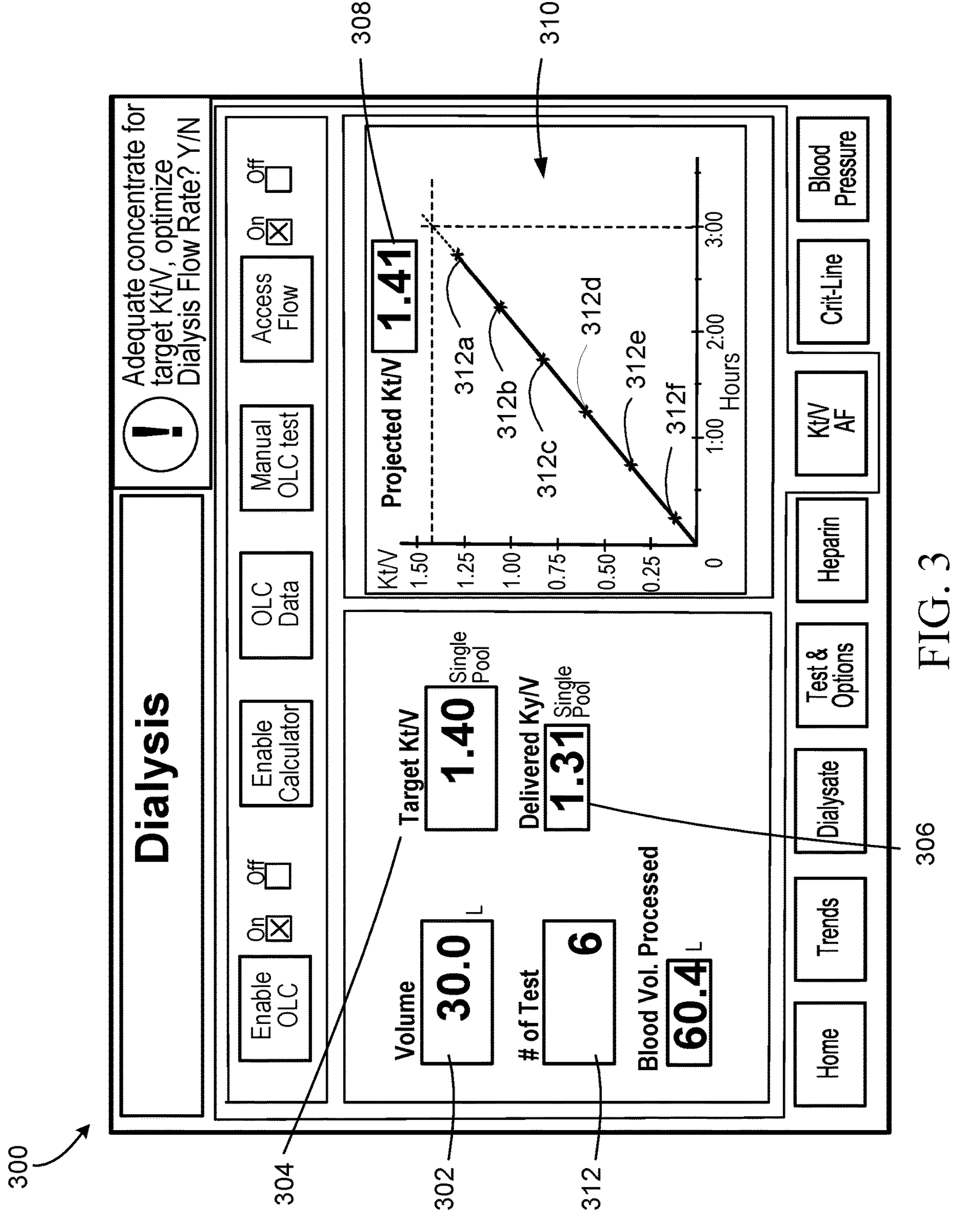
FIG. 3 is a diagram of user interface displaying a projected clearance value and a threshold clearance value.

FIG. 3 illustrates an example user interface 300 of a dialysis machine. The user interface 300 can be configured to display information related to the dialysis treatment, e.g., in addition or alternatively to the user interface 200. For example, a user input can result in changing the user interface 200 into the user interface 300.

The user interface 300 shows a volume 302 of a resource attached to the machine (e.g., a volume of a bicarbonate concentrate container, a volume of an acid container, a volume of a water container, etc.). The volume 302 can be used to determine a depletion time, as discussed above. In some implementations, the machine receives the volume, for example, from a user entry or from a sensor reading the size of a full container of the resource. For example, the full container can be labeled by its manufacturer to indicate how much material it includes. If the full container is attached to the machine before the treatment starts (i.e., at the beginning of the treatment), the machine uses such volume as the initial amount (e.g., 302) of the resource for the treatment. If a non-full container (e.g., a container that was used in a previous treatment) is attached to the machine before the treatment starts, the machine can retrieve or determine the initial amount of the resource for the current treatment based on the amount of material pulled from the container at the previous treatment. The amount of material pulled in each treatment session can be determined according to the techniques described in this disclosure (e.g., based on the full amount and the flow rate for pulling the material), and recorded in a storage medium of or in communication with the machine.

The user interface 300 also shows a threshold clearance value 304. In some implementations, the clearance threshold value can be provided by a prescription. The user interface 300 also shows a delivered (e.g., clearance) clearance value 306. The delivered clearance value 306 should not fall below the threshold clearance value 304 throughout the dialysis treatment. The delivered clearance value 306 can be determined using conductivity measurements, as discussed above.

The user interface 300 shows a projected clearance value 308 and a visual representation 310 of the projected clearance value. In some implementations, the projected clearance value can be determined via linear regression. For example, the dialysis machine can calculate a linear relationship between the delivered clearance value 306 and the time of treatment.

The user interface 300 also shows a number of clearance value measurements 312*a*, 312*b*, 312*c*, 312*d*, 312*e*, 312*f*, each measured or calculated at a respective time during the treatment. For example, in the illustrated user interface 300, six clearance value measurements 312*a*. 312*b*, 312*c*. 312*d*, 312*e*, 312*f* have been performed. At each clearance value measurement, the dialysis machine plots the delivered clearance value 306 at the time of treatment when the delivered clearance value was measured or calculated.

The multiple clearance value measurements can be used to determine a relationship between the time elapsed and the clearance value, for example, via regression (e.g., linear regression, quadratic regression, etc.). The dialysis machine can use the determined relationship to determine a projected clearance value at any particular point in future, for example, at the end of the treatment (e.g., when the prescribed treatment time has elapsed).

The projected clearance value 308 can be compared to the clearance threshold value 306 to determine whether the projected clearance value 308 meets or exceeds the clearance threshold value. If the projected clearance value 308 exceeds the clearance threshold value 306, the dialysis machine can reduce the dialysate flow rate, e.g., as discussed above. The dialysis machine can reduce the dialysate flow rate when the projected clearance value 308 exceeds the clearance threshold value 306, e.g., as discussed above. Reducing the dialysate flow rate based on the projected clearance value 308 can reduce the amount of resources spent during the treatment, e.g., to conserve resources, while also maintaining the clearance threshold value 306 from the prescription of the patient.

Figure 4:
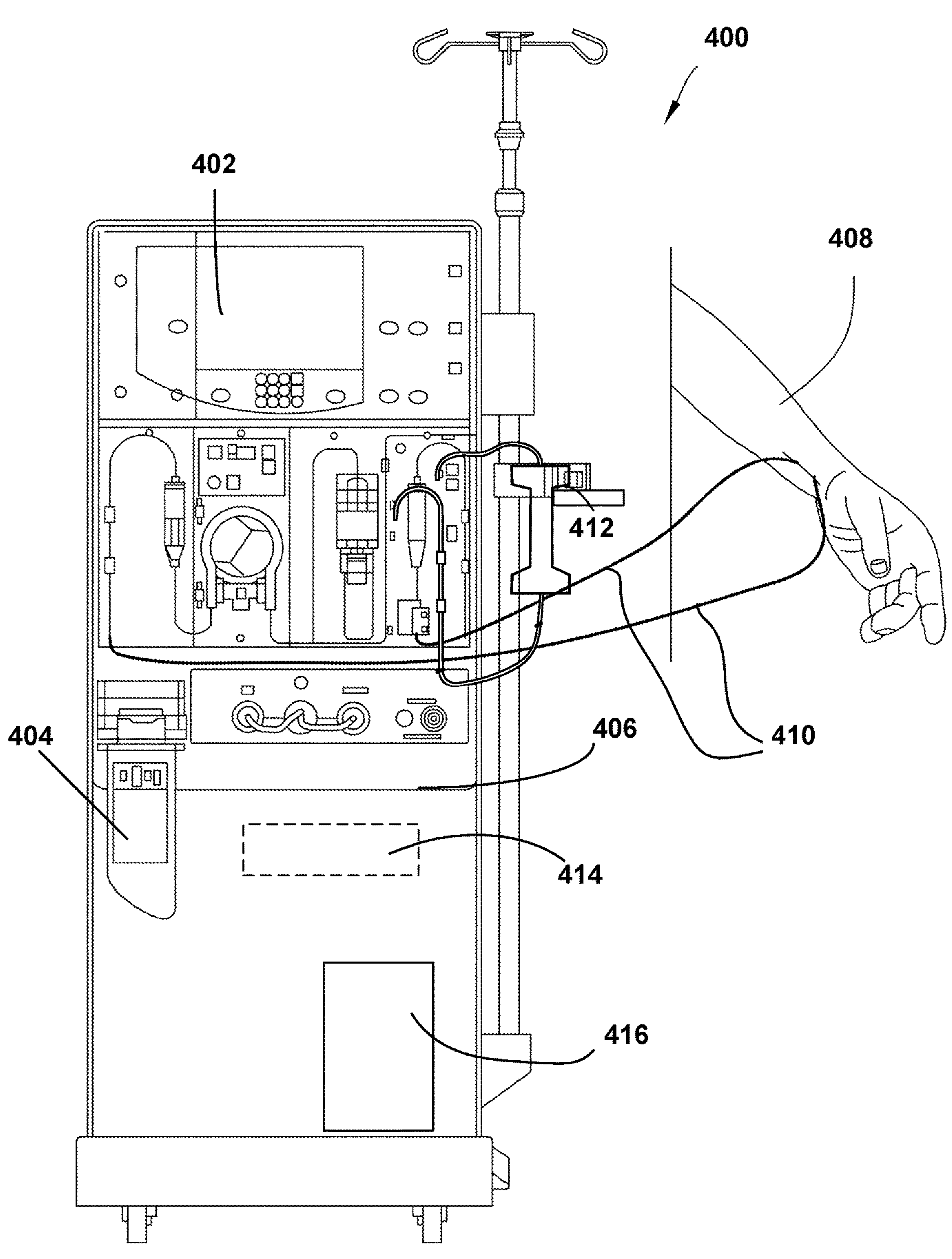
FIG. 4 is a diagram of a dialysis system during a dialysis session of a patient.

FIG. 4 illustrates an example dialysis system 400 in which a patient 408 is connected to a dialysis machine 406 using a venous bloodline 400 and an arterial bloodline 400. The system 400 shown here is an HD system, but other kinds of systems could be used. The system 400 can include any of the elements discussed with respect to FIG. 1, and can be configured to monitor and manage supply use while maintaining a desired clearance value, as discussed above.

The system 400 comprises a dialysis machine 406. Dialysis machine 406 can include several components such as supply sources 106, 108, 110, the balancing system 104, and the processor 122 explained in FIG. 1. The system 400 also includes a dialyzer 412 (e.g., dialyzer 102), a container 404, a user interface 402, a processor 414, and a fluid source 416. The dialyzer 412, dialysis machine 406, arterial and venous bloodlines 410 are in fluid communication with each other, so that an extracorporeal blood circuit is created. The extracorporeal blood circuit is supported and controlled by the processor 414, user interface 402, and further comprises a fluid source 416, and a container 404.

Blood from the patient flows from the venous bloodline into the extracorporeal blood circuit, where the blood is cleared of toxins, and flows back into the body via the arterial bloodline. While in the extracorporeal blood circuit, the blood flows through the dialyzer 412, which is configured to remove toxins and excess fluid in the blood. The dialyzer 412 is split into two chambers in which the blood of the patient flows in one direction and a dialysate produced by the dialysis machine flows in another. The two chambers are separated by a semipermeable membrane. Toxins and excess fluid move from the blood to the dialysate chamber, often due to a concentration gradient. The dialysate is produced by mixing the contents of the containers with additional fluid and substances. The concentrations and flow rates of the dialysis are prescribed by a medical professional. Different concentrations and flow rates can vary the length of treatment and impact on the patient. For example, a high flow rate may result in a shorter treatment time but may be more difficult for the patient.

The container is connectable and disconnectable from the dialysis machine. The container is connected to the machine via connecting lines and tubes. Some of the tubes connected to the container are responsible for adding or removing fluid into and from the container. The dialysis machine is configured to connect lines and tubes of the dialysis machine to a connector on the container. The connector is similar for every volume of container provided, allowing for similar connection attachment procedures regardless of the container volume. Multiple container volumes are available to the operator. For example, the dialysis machine may connect to containers with volumes of 650 mg and 900 mg.

Figure 5:
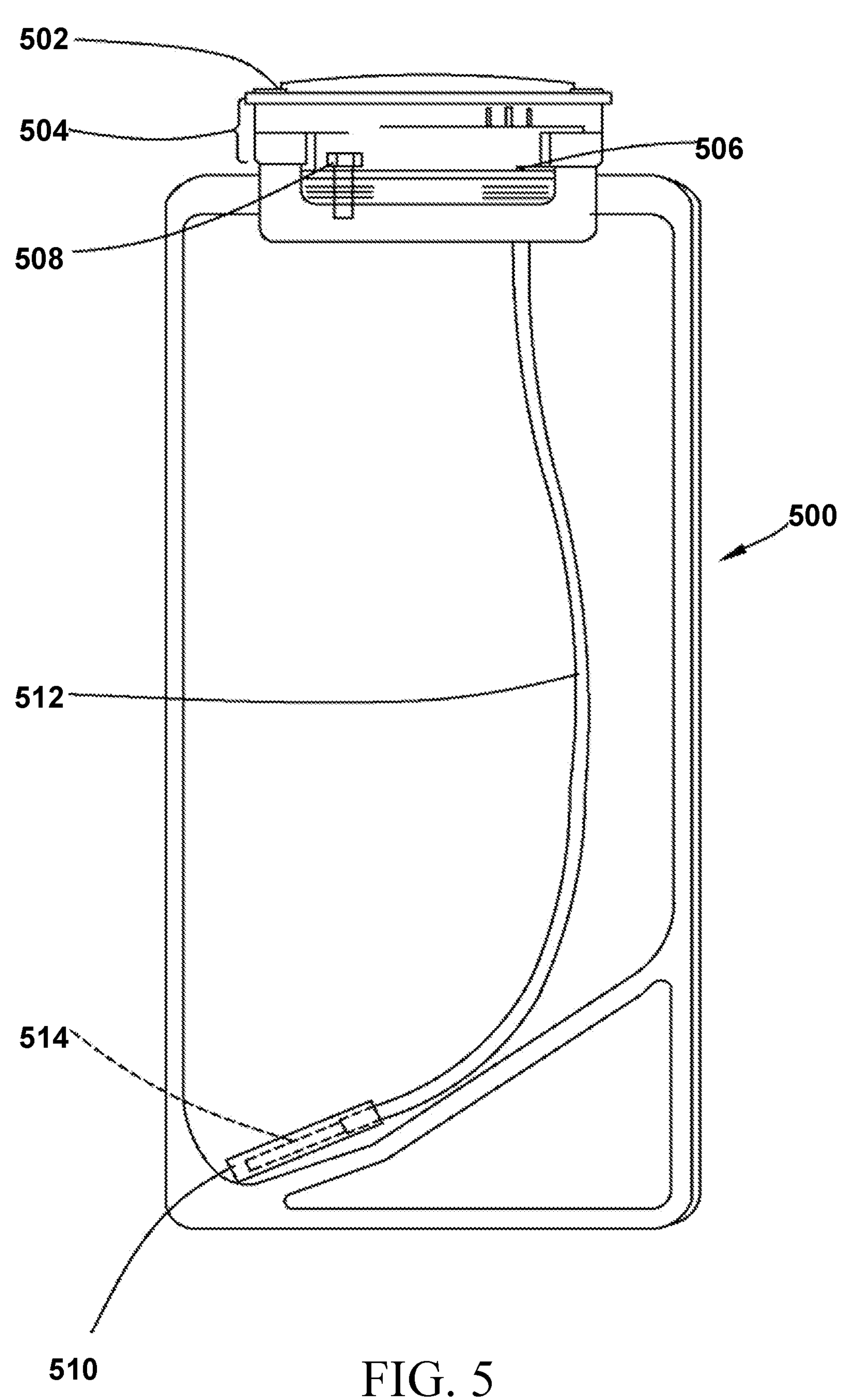
FIG. 5 is a diagram of a container connected to a dialysis machine within a dialysis system.

FIG. 5 illustrates a container 500 (e.g., bicarbonate source 106) configured to be inserted into the dialysis machine 406 and containing a substance. The container can include a substance, such as bicarbonate liquid or powder, to be used during the dialysis treatment. For example, the substance can be a powder concentrate that is dissolvable with a fluid to create a saturated solution.

The dialysis machine 406 is configured to create a saturated solution by flowing fluid into the container 500, via an inlet 508 that is integrated into the connector 504 of the container 500. The inlet 504 also connects to a fluid source. The dialysis machine is also configured to remove the saturated fluid from the container 500 via an outlet 506 integrated into the connector 504, and transport it to a location for mixing with other substances. After being removed from the container, the saturated solution mixes with additional solutions to create a dialysate or other dialysis fluid. The dialysate then flows through the dialyzer to clear the blood of toxins, and is expelled into a waste receptacle.

To prepare the dialysis machine, the operator inserts the container 500 into the dialysis machine 406, connecting the connector 504 of the cap 502 to the fluid line of the dialysis machine 406. The connector 504 facilitates the connection of the inlet 508 port to the fluid source 416 and facilitates the connection of the outlet 506 port to the dialyzer 412. The fluid source 416 provides temperature appropriate fluid for mixing. A warm fluid may allow for improved dissolution and a more saturated solution.

The fluid flows into the container 500 from the inlet 508. The inlet 508 is in communication a pressure sensor (not shown) that is configured to measure the pressure within the container 500. Once the pressure sensor measures a predetermined pressure, the container 500 is identified as full by the processor. The processor sends a signal to a fluid source pump (not shown) disposed upstream of the inlet 508 and/or a fluid valve (not shown) disposed upstream of the inlet 508, to stop fluid flow into the container 500. The fluid valve may prevent fluid flow by impeding the fluid line upstream of the inlet 508 such that fluid may not pass into the container 500. The fluid stops entering at the inlet 508.

After fluid in-flow stops, the fluid is drawn from the container 504 through an opening 510 of a tube 512 connected to the outlet 506. The opening 510 is covered by a filter 514 to ensure only fluid is removed from the container 500. The saturated fluid continues along the fluid line to combine with other substances to produce dialysate. In some implementations, the substance within the container 500 is bicarbonate. In some implementations, the substance is an acid compound used in dialysis. In some implementations, the substance within the container 500 is a liquid concentrate.

Figure 6:
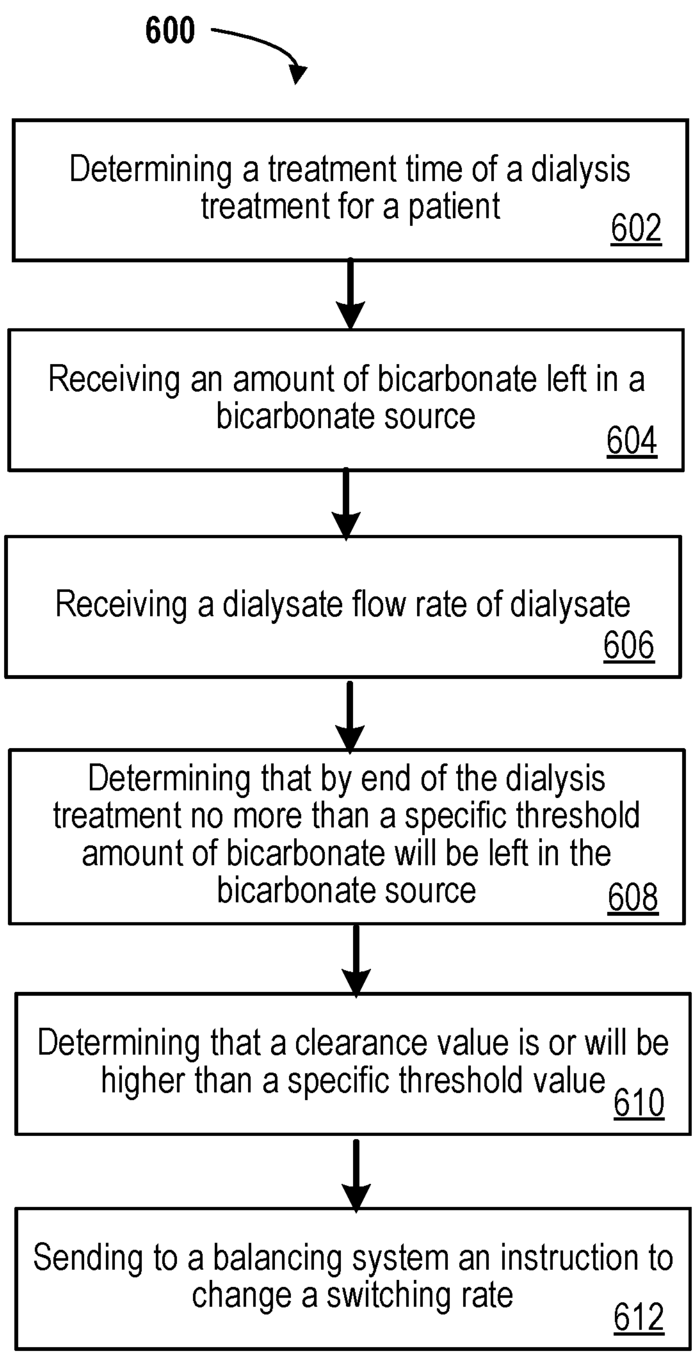
FIG. 6 is a flow diagram for an example method of performing dialysis.

FIG. 6 is a flowchart of an example process 600 of performing dialysis. Process 600 can be performed by a processor of a dialysis machine, for example, processor 122 shown in FIG. 1. The process 600 includes determining a treatment time of a dialysis treatment for a patient (602). For example, the treatment time can be based on a prescription received from an external source, e.g., the patient. In some implementations, user input can provide the prescription.

Process 600 can also include receiving or determining an amount of bicarbonate left in a bicarbonate source attached to the dialysis machine (604), e.g., an initial amount of bicarbonate before the treatment starts. The processor can receive an amount of bicarbonate from a first sensor or through an operator's input. The first sensor can include, e.g., a pressure sensor and/or an ultrasound sensor. In case of using a full container, the sensor can be a read sensor that reads a label on the source to determine the volume of the container as filled by its manufacturer. In case of using a container that was used at a prior treatment, the processor can subtract the full volume to the volume that was pulled from the container during the prior treatment to determine the amount of bicarbonate left in the source. In some implementations, the processor determines the amount of bicarbonate left in the bicarbonate source based on signals received from the first sensor.

Process 600 also includes receiving a dialysate flow rate of dialysate running in the machine (606). For example, the processor can receive a dialysate flow rate from a second sensor. The second sensor can include, e.g., a flow rate sensor. In some implementations, the processor determines the dialysate flow rate based on signals received from the second sensor. The dialysate can include bicarbonate pumped out of the bicarbonate source.

Process 600 continues with determining that by the end of the dialysis treatment, no more than a specific threshold amount of bicarbonate will be left in the bicarbonate source (608). For example, the processor can predict that no more than a specific threshold of bicarbonate will be left in the bicarbonate source based on the treatment time, the amount of bicarbonate left in the bicarbonate source, and the dialysate flow rate. The processor can use the dialysate flow rate to determine the rate at which bicarbonate is leaving the bicarbonate source. The processor can then use the treatment time and the rate at which the bicarbonate is leaving the bicarbonate source to determine how much bicarbonate will leave the bicarbonate source by the end of the treatment time. The processor can subtract the amount of bicarbonate that will leave the bicarbonate source from the amount of bicarbonate left in the bicarbonate source to determine how much bicarbonate will be left by the end of treatment.

In some implementations, the processor determines whether no more than a specific threshold of bicarbonate will be left in the bicarbonate source. In some implementations, the threshold amount can be preset by the operations of the dialysis machine (e.g., a default threshold amount). In some implementations, the threshold amount can be set by a user. For example, the threshold amount can be set to zero. In some implementations, the threshold amount can be set to a minimum amount of bicarbonate used for a post-treatment process. A post-treatment process can include running fluids (e.g., water, bicarbonate solution, etc.) through the dialysis machine to clean up residues left from treating the current patient before starting to treat the next patient.

Process 600 continues with determining that a clearance value is or will be higher than a specific threshold value (610). For example, determining that a clearance value is higher than a specific threshold value can refer to determining that a current clearance value is higher than a specific threshold value. For example, the processor can receive measurements of respective conductivity values of the dialysate and calculate a current clearance value based on the received conductivity values. Determining that a clearance value will be higher than a specific threshold value refers to determining that a projected future value is higher than a specific threshold value. The processor can predict a future clearance value for a time at or before the treatment ends. For example, the processor can predict a future clearance value based on a trend in multiple clearance values and the current clearance value. The trend in the multiple clearance values and the current clearance value can be determined, e.g., via regression (e.g., linear regression, quadratic regression, etc.) as described above. The trend in the multiple measured clearance values can be used to predict the future clearance value.

The specific clearance threshold value can be determined from the prescription of the patient. If the predicted future clearance value is greater than the specific threshold clearance value, the processor can determine that the predicted future clearance value is higher than the specific clearance threshold value.

In response to determining that a clearance value is or will be higher than a specific threshold value, the process 600 continues with sending an instruction to a balancing system to change a switching rate (612). For example, the instruction can change the switching rate to reduce the dialysate flow rate to a reduced rate. In some implementations, the processor can send the instruction to a switch on the balancing system to reduce the dialysate flow rate so that the projected clearance value meets the clearance threshold value. Meeting or being substantially close to (e.g., within a predetermined range, e.g., within 5% of the clearance threshold value, rather than exceeding the clearance threshold value, can provide a treatment that matches the prescription of the patient while conserving the resources of the dialysis treatment (e.g., water, acid, bicarbonate concentrate, and other chemicals) reducing the dialysis flow rate reduces the amount of dialysate used during the treatment. Reducing the amount of dialysate used during the treatment reduces the amount of resources used to form the dialysate. For example, reducing the amount of dialysate can reduce the rate of bicarbonate pumped out of the bicarbonate source while maintaining a clearance value at no less than the clearance threshold value.

If the predicted clearance value is less than the specific threshold clearance value, the processor can determine that the predicted future clearance value is less than the specific clearance threshold value. The processor can then send an instruction to change a switching rate to increase the dialysate flow rate to an increased rate. For example, the processor can send an instruction to a balancing system that receives the dialysate, as discussed above. In some implementations, the processor can send an instruction to the switch to increase the dialysate flow rate so that the projected clearance value meets (or as noted above, be within a predefined range of) the clearance threshold value. The projected clearance value can be increased so that the dialysis treatment satisfies the requirements specified in the patient's prescription.

In some implementations, the processor can determine that the treatment has ended and the machine has been detached from the patient. For example, the processor can determine that treatment has ended based on sensor measurements that indicate a change of pressure on the tubing that is attached to the patient during treatment or indicate a significant reduction (e.g., a stop) in blood flow rate flowing through the dialyzer. In some implementations, the processor can send a post-treatment instruction to reduce the dialysate flow rate. For example, the processor can send a post-treatment instruction to a balancing system to reduce the dialysate flow rate to less than half of a current dialysate flow rate.

Implementations of the subject matter and the functional operations described above can be implemented in various types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

While this specification includes many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some examples be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations. Also it should be understood that the described program components and systems may generally be integrated together in a single software product or packaged into multiple software products.

A number of embodiments of the invention have been described. Nevertheless, it will be understood that various modifications may be made without departing from the spirit and scope of the invention. For example, various forms of the flows shown above may be used, with steps re-ordered, added, or removed. Accordingly, other implementations are within the scope of the following claims.

What is claimed:

1. A computer-implemented method executable automatically by one or more processors of a dialysis machine, the method comprising:

determining, based on a prescription received from an external source, a treatment time of a dialysis treatment for a patient;

receiving, from at least a sensor of the dialysis machine, a dialysate flow rate of dialysate running in the dialysis machine, the dialysate comprising bicarbonate pumped out of a bicarbonate source attached to the dialysis machine, wherein the bicarbonate source has an initial amount of bicarbonate before the dialysis treatment starts; and predicting, based on (i) the treatment time, (ii) the initial amount of bicarbonate, and (iii) the dialysate flow rate, that by end of the dialysis treatment no more than a specific threshold amount of bicarbonate will be left in the bicarbonate source, and in response, determining that a clearance value during the dialysis treatment is or will be higher than a specific threshold clearance value, wherein the clearance value is determined based on a urea clearance, time, and an inverse of a volume of fluid passing through a fluid line over time, and changing a switching rate of a balancing system of the dialysis machine to reduce the dialysate flow rate to a reduced rate, thereby reducing a rate of bicarbonate pumped out of the bicarbonate source while maintaining a clearance value of the dialysis treatment at no less than the specific threshold clearance value.

2. The method of claim 1, wherein the determined clearance value is or is determined based on a current clearance value of the dialysis treatment, and the method further comprises determining the current clearance value by:

receiving, from multiple sensors, measurements of respective conductivity values of the dialysate running to or from a dialyzer of the dialysis machine; and calculating the current clearance value based on the received conductivity values.

3. The method of claim 1, wherein the determined clearance value is a future clearance value, and the method further comprises predicting the future clearance value by:

calculating multiple clearance values for the dialysis treatment over a time period during the dialysis treatment, each clearance value in the multiple clearance values being calculated based on respective conductivity values of the dialysate at a respective time during the time period, and predicting, based on a trend in the multiple clearance values and a current clearance value of the dialysis treatment, the future clearance value for a time before the dialysis treatment ends.

4. The method of claim 3, further comprising changing the switching rate of the balancing system based on the predicted future clearance value, wherein changing the switching rate includes sending a reduction value in the switching rate to the balancing system, wherein the reduction value depends on a difference between the predicted future clearance value and the specific threshold clearance value such that a higher difference causes a higher reduction value.

5. The method of claim 3, wherein the method further comprises:

determining that the predicted future clearance value is less than the specific clearance threshold value, and in response, changing the switching rate of the balancing system a second time to increase the dialysate flow rate so that the clearance value of the dialysis treatment increases.

6. The method of claim 3, further comprising sending the predicted future clearance value to be presented on a display.

7. The method of claim 1, wherein changing the switching rate of the balancing system comprises sending a rate reduction amount for the switching rate to the balancing system.

8. The method of claim 1, further comprising:

determining that the dialysis treatment has ended and the dialysis machine has been detached from the patient, and in response, sending, to the balancing system, a post-treatment instruction to reduce the dialysate flow rate.

9. The method of claim 8, wherein the post-treatment instruction includes an instruction to reduce the dialysate flow rate to less than half.

10. A dialysis system comprising:

a dialyzer;

a fluid line for passing dialysate from bicarbonate source to a balancing system;

a sensor configured to measure a dialysate flow rate of dialysate running in the fluid line, the dialysate comprising bicarbonate pumped out of the bicarbonate source;

the balancing system configured to transfer clean dialysate from the fluid line to the dialyzer, and drain used dialysate from the dialyzer to a drainage, wherein the balancing system comprises a switch with a status that changes with a switching rate, wherein a change in the switch rate causes a change in the dialysis flow rate running through the fluid line; and a processor configured to perform automatic operations comprising:

determining, based on a prescription received from an external source, a treatment time of a dialysis treatment for a patient, receiving, from the sensor, the dialysate flow rate, wherein the bicarbonate source has an initial amount of bicarbonate before the dialysis treatment starts, predicting, based on (i) the treatment time, (ii) the initial amount of bicarbonate, and (iii) the dialysate flow rate, that by end of the dialysis treatment no more than a specific threshold amount of bicarbonate will be left in the bicarbonate source, and in response, determining that a clearance value during the dialysis treatment is or will be higher than a specific threshold clearance value, wherein the clearance value is determined based on a urea clearance, time, and an inverse of a volume of fluid passing through a fluid line over the time, and changing the switching rate of the balancing system to reduce the dialysate flow rate to a reduced rate, thereby reducing a rate of bicarbonate pumped out of the bicarbonate source while maintaining a clearance value of the dialysis treatment at no less than the specific threshold clearance value.

11. The dialysis system of claim 10, further comprising multiple sensors operatively connected to the fluid line, the multiple sensors being configured to measure respective conductivity values of the dialysate running to or from the dialyzer.

12. The dialysis system of claim 11, wherein the determined clearance value is or is determined based on a current clearance value of the dialysis treatment, and the operations further comprise determining the current clearance value by:

receiving, from the multiple sensors, the respective conductivity values; and calculating the current clearance value based on the received conductivity values.

13. The dialysis system of claim 10, wherein the determined clearance value is a future clearance value, and the operations further comprise predicting the future clearance value by:

calculating multiple clearance values for the dialysis treatment over a time period during the dialysis treatment, each clearance value in the multiple clearance values being calculated based on respective conductivity values of the dialysate at a respective time during the time period; and predicting, based on a trend in the multiple clearance values and a current clearance value of the dialysis treatment, the future clearance value for a time before the dialysis treatment ends.

14. The dialysis system of claim 13, wherein the operations further comprise changing the switching rate based on the predicted future clearance value, wherein changing the switching rate includes sending a reduction value in the switching rate to the balancing system, wherein the reduction value depends on a difference between the predicted future clearance value and the specific threshold clearance value such that a higher difference causes a higher reduction value.

15. The dialysis system of claim 13, wherein the operations further comprise:

determining that the predicted future clearance value is less than the specific threshold clearance value, and in response; and changing the switching rate a second time to increase the dialysate flow rate so that the clearance value of the dialysis treatment increases.

16. The dialysis system of claim 13, wherein the operations further comprise sending the predicted future clearance value to display to be presented on the display.

17. The dialysis system of claim 10, wherein changing the switching rate comprises sending a rate reduction amount for the switching rate to the balancing system.

18. One or more computer readable media storing instructions that are automatically executable by a processing device, and upon such execution cause the processing device to perform operations comprising:

determining, based on a prescription received for a patient from an external source, a treatment time of a dialysis treatment for the patient;

receiving, from at least a sensor of a dialysis machine, a dialysate flow rate of dialysate running in the dialysis machine, the dialysate comprising bicarbonate pumped out of a bicarbonate source attached to the dialysis machine, wherein the bicarbonate source has an initial amount of bicarbonate before the dialysis treatment starts;

predicting, based on (i) the treatment time, (ii) the initial amount of bicarbonate, and (iii) the dialysate flow rate, that by end of the dialysis treatment no more than a specific threshold amount of bicarbonate will be left in the bicarbonate source, and in response, determining that a clearance value during the dialysis treatment is or will be higher than a specific threshold clearance value, wherein the clearance value is determined based on a urea clearance, time, and an inverse of a volume of fluid passing through the fluid over the time, and changing a switching rate of a balancing system of the dialysis machine to reduce the dialysate flow rate to a reduced rate thereby reducing a rate of bicarbonate pumped out of the bicarbonate source while maintaining a clearance value of the dialysis treatment at no less than the specific threshold clearance value.

19. The computer readable media storing instructions of claim 18, wherein the determined clearance value is a future clearance value, and the operations further comprises predicting the future clearance value by:

calculating multiple clearance values for the dialysis treatment over a time period during the dialysis treatment, each clearance value in the multiple clearance values being calculated based on respective conductivity values of the dialysate at a respective time during the time period; and predicting, based on a trend in the multiple clearance values and a current clearance value of the dialysis treatment, the future clearance value for a time before the dialysis treatment ends.

20. The computer readable media storing instructions of claim 19, wherein the operations further comprise:

changing the switching rate based on the predicted future clearance value, wherein changing the switching rate comprises sending a reduction value in the switching rate to the balancing system, wherein the reduction value depends on a difference between the predicted future clearance value and the specific threshold clearance value such that a higher difference causes a higher reduction value.

* * * * *